United States Patent
Buss et al.

(10) Patent No.: US 8,828,056 B2
(45) Date of Patent: Sep. 9, 2014

(54) ROD TO ROD CROSS CONNECTOR

(75) Inventors: Donald A. Buss, Macungie, PA (US);
Tyler Haskins, Conshohocken, PA (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 124 days.

(21) Appl. No.: 13/447,617

(22) Filed: Apr. 16, 2012

(65) Prior Publication Data
US 2013/0274801 A1 Oct. 17, 2013

(51) Int. Cl.
*A61B 17/70* (2006.01)
(52) U.S. Cl.
USPC ............ 606/251; 606/250; 606/278
(58) Field of Classification Search
USPC ............ 606/71, 250–253, 260, 278
See application file for complete search history.

(56) References Cited

U.S. PATENT DOCUMENTS

| | | |
|---|---|---|
| 3,865,105 A | 2/1975 | Lode |
| 4,349,017 A | 9/1982 | Sayegh |
| 4,361,144 A | 11/1982 | Slatis |
| 4,483,334 A | 11/1984 | Murray |
| 4,648,388 A | 3/1987 | Steffee |
| 4,719,905 A | 1/1988 | Steffee |
| 4,747,400 A | 5/1988 | Koeneman |
| 4,768,524 A | 9/1988 | Hardy |
| 4,794,918 A | 1/1989 | Wolter |
| 4,944,743 A | 7/1990 | Gotzen |
| 5,002,542 A | 3/1991 | Frigg |
| 5,005,562 A | 4/1991 | Cotrel |
| 5,030,220 A | 7/1991 | Howland |
| 5,053,034 A | 10/1991 | Olerud |
| 5,074,864 A | 12/1991 | Cozad |
| 5,084,048 A | 1/1992 | Jacob |
| 5,084,049 A | 1/1992 | Asher |
| 5,098,432 A | 3/1992 | Wagenknecht |
| 5,102,412 A | 4/1992 | Rogozinski |
| 5,112,332 A | 5/1992 | Cozad |
| 5,116,334 A | 5/1992 | Cozad |
| 5,147,359 A | 9/1992 | Cozad |
| 5,154,718 A | 10/1992 | Cozad |
| 5,176,678 A | 1/1993 | Tsou |
| 5,181,917 A | 1/1993 | Rogozinski |
| 5,196,013 A | 3/1993 | Harms |
| 5,201,374 A | 4/1993 | Rahm |

(Continued)

FOREIGN PATENT DOCUMENTS

| | | |
|---|---|---|
| DE | 3924050 A1 | 1/1991 |
| DE | 29808593 U1 | 10/1999 |

(Continued)

*Primary Examiner* — Pedro Philogene
*Assistant Examiner* — Christina Negrellirodrigue
(74) *Attorney, Agent, or Firm* — RatnerPrestia

(57) ABSTRACT

A cross connector for connecting elongated fixation elements, such as spinal fixation rods, includes a central body and one or more actuators. The rod to rod connector may include a first lever and a second lever coupled to the central body. The first lever may include a free end separated from the central body by a first channel. The second lever may include a free end separated from the central body by a second channel. The one or more actuators may be operable to pivot the first and second levers into a relatively closed position. When the first and second levers are in the relatively closed position, the free ends of the first and second levers are moved toward one another and toward the central body to contract the first and second channels.

35 Claims, 4 Drawing Sheets

(56) References Cited

U.S. PATENT DOCUMENTS

| | | |
|---|---|---|
| 5,207,678 A | 5/1993 | Harms |
| 5,254,118 A | 10/1993 | Mirkovic |
| 5,257,993 A | 11/1993 | Asher |
| 5,261,907 A | 11/1993 | Vignaud |
| 5,261,913 A | 11/1993 | Marnay |
| 5,275,600 A | 1/1994 | Allard |
| 5,304,179 A | 4/1994 | Wagner |
| 5,306,275 A | 4/1994 | Bryan |
| 5,312,405 A | 5/1994 | Korotko |
| 5,330,473 A | 7/1994 | Howland |
| 5,334,203 A | 8/1994 | Wagner |
| 5,352,224 A | 10/1994 | Westermann |
| 5,374,267 A | 12/1994 | Siegal |
| 5,380,325 A | 1/1995 | Lahille |
| 5,382,248 A | 1/1995 | Jacobson |
| 5,395,370 A | 3/1995 | Muller |
| 5,397,363 A | 3/1995 | Gelbard |
| 5,403,316 A | 4/1995 | Ashman |
| 5,413,602 A | 5/1995 | Metz-Stavenhagen |
| 5,437,669 A | 8/1995 | Yuan |
| 5,468,241 A | 11/1995 | Metz-Stavenhagen |
| 5,470,333 A | 11/1995 | Ray |
| 5,474,555 A | 12/1995 | Puno |
| 5,476,464 A | 12/1995 | Metz-Stavenhagen |
| 5,487,742 A | 1/1996 | Cotrel |
| 5,498,263 A | 3/1996 | DiNello |
| 5,507,745 A | 4/1996 | Logroscino |
| 5,507,746 A | 4/1996 | Lin |
| 5,514,132 A | 5/1996 | Csernatony |
| 5,522,816 A | 6/1996 | Dinello |
| 5,527,314 A | 6/1996 | Brumfield |
| 5,531,745 A | 7/1996 | Ray |
| 5,531,747 A | 7/1996 | Ray |
| 5,534,002 A | 7/1996 | Brumfield |
| 5,536,268 A | 7/1996 | Griss |
| 5,545,164 A | 8/1996 | Howland |
| 5,545,166 A | 8/1996 | Howland |
| 5,545,167 A | 8/1996 | Lin |
| 5,549,607 A | 8/1996 | Olson |
| 5,562,660 A | 10/1996 | Grob |
| 5,562,662 A | 10/1996 | Brumfield |
| 5,562,663 A | 10/1996 | Wisnewski |
| 5,569,246 A | 10/1996 | Ojima |
| 5,569,247 A | 10/1996 | Morrison |
| 5,601,552 A | 2/1997 | Cotrel |
| 5,609,594 A | 3/1997 | Errico |
| 5,609,992 A | 3/1997 | Sorori |
| 5,611,800 A | 3/1997 | Davis |
| 5,613,968 A | 3/1997 | Lin |
| 5,620,444 A | 4/1997 | Assaker |
| 5,624,442 A | 4/1997 | Mellinger |
| 5,630,816 A | 5/1997 | Kambin |
| 5,643,259 A | 7/1997 | Sasso |
| 5,651,789 A | 7/1997 | Cotrel |
| 5,653,708 A | 8/1997 | Howland |
| 5,667,506 A | 9/1997 | Sutterlin |
| 5,667,507 A | 9/1997 | Corin |
| 5,669,910 A | 9/1997 | Korhonen |
| 5,672,176 A | 9/1997 | Biedermann |
| 5,676,665 A | 10/1997 | Bryan |
| 5,676,703 A | 10/1997 | Gelbard |
| 5,683,393 A | 11/1997 | Ralph |
| 5,688,272 A | 11/1997 | Montague |
| 5,688,275 A | 11/1997 | Koros |
| 5,702,452 A | 12/1997 | Argenson |
| 5,707,372 A | 1/1998 | Errico |
| 5,709,684 A | 1/1998 | Errico |
| 5,709,685 A | 1/1998 | Dombrowski |
| 5,716,355 A | 2/1998 | Jackson |
| 5,716,356 A | 2/1998 | Biedermann |
| 5,727,899 A | 3/1998 | Dobrovolny |
| 5,733,285 A | 3/1998 | Errico |
| 5,733,286 A | 3/1998 | Errico |
| 5,735,850 A | 4/1998 | Baumgartner |
| 5,735,851 A | 4/1998 | Errico |
| 5,735,853 A | 4/1998 | Olerud |
| 5,741,254 A | 4/1998 | Henry |
| 5,741,255 A | 4/1998 | Krag |
| 5,743,911 A | 4/1998 | Cotrel |
| 5,746,741 A | 5/1998 | Kraus |
| 5,752,955 A | 5/1998 | Errico |
| 5,800,548 A | 9/1998 | Martin |
| 5,810,816 A | 9/1998 | Roussouly |
| 5,814,046 A | 9/1998 | Hopf |
| 5,876,403 A | 3/1999 | Shitoto |
| 5,885,284 A | 3/1999 | Errico |
| 5,899,903 A | 5/1999 | Cotrel |
| 5,928,231 A | 7/1999 | Klein |
| 5,938,663 A | 8/1999 | Petreto |
| 5,947,965 A | 9/1999 | Bryan |
| 5,947,966 A | 9/1999 | Drewry |
| 5,947,967 A | 9/1999 | Barker |
| 5,976,133 A | 11/1999 | Kraus |
| 5,976,135 A | 11/1999 | Sherman |
| 5,980,521 A | 11/1999 | Montague |
| 5,980,523 A | 11/1999 | Jackson |
| 5,984,922 A | 11/1999 | McKay |
| 5,984,923 A | 11/1999 | Breard |
| 5,984,924 A | 11/1999 | Asher |
| 5,989,250 A | 11/1999 | Wagner |
| 5,989,251 A | 11/1999 | Nichols |
| 5,997,539 A | 12/1999 | Errico |
| 6,027,533 A | 2/2000 | Olerud |
| 6,030,388 A | 2/2000 | Yoshimi |
| 6,050,997 A | 4/2000 | Mullane |
| 6,063,090 A | 5/2000 | Schlapfer |
| 6,077,262 A | 6/2000 | Schlapfer |
| 6,080,156 A | 6/2000 | Asher |
| 6,083,226 A | 7/2000 | Fiz |
| 6,090,110 A | 7/2000 | Metz-Stavenhagen |
| 6,096,039 A | 8/2000 | Stoltenberg |
| 6,110,173 A | 8/2000 | Thomas |
| 6,113,600 A | 9/2000 | Drummond |
| 6,113,601 A | 9/2000 | Tatar |
| 6,132,430 A | 10/2000 | Wagner |
| 6,136,003 A | 10/2000 | Hoeck |
| 6,139,548 A | 10/2000 | Errico |
| 6,171,311 B1 | 1/2001 | Richelsoph |
| 6,176,861 B1 | 1/2001 | Bernstein |
| 6,179,838 B1 | 1/2001 | Fiz |
| 6,179,841 B1 | 1/2001 | Jackson |
| 6,183,473 B1 | 2/2001 | Ashman |
| 6,187,005 B1 | 2/2001 | Brace |
| 6,210,413 B1 | 4/2001 | Justis |
| 6,214,006 B1 | 4/2001 | Metz-Stavenhagen |
| 6,217,578 B1 | 4/2001 | Crozet |
| 6,231,575 B1 | 5/2001 | Krag |
| 6,234,705 B1 | 5/2001 | Troxell |
| 6,238,396 B1 | 5/2001 | Lombardo |
| 6,254,602 B1 | 7/2001 | Justis |
| 6,254,603 B1 | 7/2001 | Gertzbein |
| 6,258,090 B1 | 7/2001 | Jackson |
| 6,261,287 B1 | 7/2001 | Metz-Stavenhagen |
| 6,264,658 B1 | 7/2001 | Lee |
| 6,267,765 B1 | 7/2001 | Taylor |
| 6,273,888 B1 | 8/2001 | Justis |
| 6,280,442 B1 | 8/2001 | Barker |
| 6,280,443 B1 | 8/2001 | Gu |
| 6,280,445 B1 | 8/2001 | Morrison |
| 6,283,967 B1 | 9/2001 | Troxell |
| 6,287,308 B1 | 9/2001 | Betz |
| 6,287,309 B1 | 9/2001 | Baccelli |
| 6,287,311 B1 | 9/2001 | Sherman |
| 6,290,700 B1 | 9/2001 | Schmotzer |
| 6,290,703 B1 | 9/2001 | Ganem |
| 6,299,614 B1 | 10/2001 | Kretschmer |
| 6,302,882 B1 | 10/2001 | Lin |
| 6,302,888 B1 | 10/2001 | Mellinger |
| 6,306,137 B2 | 10/2001 | Troxell |
| 6,309,135 B1 | 10/2001 | Thomson |
| 6,309,390 B1 | 10/2001 | Le Couedic |
| 6,309,391 B1 | 10/2001 | Crandall |
| 6,326,740 B1 | 12/2001 | Chang |
| 6,328,740 B1 | 12/2001 | Richelsoph |

(56) References Cited

U.S. PATENT DOCUMENTS

| | | |
|---|---|---|
| 6,328,741 B1 | 12/2001 | Richelsoph |
| 6,361,535 B2 | 3/2002 | Jackson |
| 6,368,319 B1 | 4/2002 | Schaefer |
| 6,368,321 B1 | 4/2002 | Jackson |
| 6,371,957 B1 | 4/2002 | Amrein |
| 6,375,657 B1 | 4/2002 | Doubler |
| 6,379,354 B1 | 4/2002 | Rogozinski |
| 6,379,357 B1 | 4/2002 | Bernstein |
| 6,402,751 B1 | 6/2002 | Hoeck |
| 6,443,953 B1 | 9/2002 | Perra |
| 6,458,132 B2 | 10/2002 | Choi |
| 6,471,705 B1 | 10/2002 | Biedermann |
| 6,524,310 B1 | 2/2003 | Lombardo |
| 6,537,276 B2 | 3/2003 | Metz-Stavenhagen |
| 6,554,832 B2 | 4/2003 | Shluzas |
| 6,565,568 B1 | 5/2003 | Rogozinski |
| 6,565,569 B1 | 5/2003 | Assaker |
| 6,569,164 B1 | 5/2003 | Assaker |
| 6,572,618 B1 | 6/2003 | Morrison |
| 6,574,789 B1 | 6/2003 | Yamauchi |
| 6,602,253 B2 | 8/2003 | Richelsoph |
| 6,610,063 B2 | 8/2003 | Kumar |
| 6,616,668 B2 | 9/2003 | Altarac |
| 6,618,960 B2 | 9/2003 | Brown |
| 6,620,164 B2 | 9/2003 | Ueyama |
| 6,626,908 B2 | 9/2003 | Cooper |
| 6,652,535 B2 | 11/2003 | Kvarnstrom |
| 6,673,073 B1 | 1/2004 | Schäfer |
| 6,685,705 B1 | 2/2004 | Taylor |
| 6,699,248 B2 | 3/2004 | Jackson |
| 6,736,816 B2 | 5/2004 | Ritland |
| 6,736,817 B2 | 5/2004 | Troxell |
| 6,736,820 B2 | 5/2004 | Biedermann |
| 6,740,086 B2 | 5/2004 | Richelsoph |
| 6,749,361 B2 | 6/2004 | Hermann |
| 6,749,612 B1 | 6/2004 | Conchy |
| 6,749,613 B1 | 6/2004 | Conchy |
| 6,758,545 B2 | 7/2004 | Ikeda |
| 6,770,075 B2 | 8/2004 | Howland |
| 6,773,214 B2 | 8/2004 | Jakubowski |
| 6,783,526 B1 | 8/2004 | Lin |
| 6,786,907 B2 | 9/2004 | Lange |
| 6,872,208 B1 | 3/2005 | McBride |
| 6,872,209 B2 | 3/2005 | Morrison |
| 6,875,211 B2 | 4/2005 | Nichols |
| 6,887,241 B1 | 5/2005 | McBride |
| 6,960,212 B2* | 11/2005 | Richelsoph et al. .......... 403/342 |
| 6,964,665 B2 | 11/2005 | Thomas |
| 7,008,423 B2 | 3/2006 | Assaker |
| 7,033,358 B2 | 4/2006 | Taylor |
| 7,081,116 B1 | 7/2006 | Carly |
| 7,112,036 B2 | 9/2006 | Lubell |
| 7,122,036 B2 | 10/2006 | Vanacker |
| 7,128,743 B2 | 10/2006 | Metz-Stavenhagen |
| 7,137,986 B2 | 11/2006 | Troxell |
| 7,166,108 B2 | 1/2007 | Mazda |
| 7,270,665 B2 | 9/2007 | Morrison |
| 7,314,467 B2 | 1/2008 | Howland |
| 7,322,979 B2 | 1/2008 | Crandall |
| 7,717,938 B2* | 5/2010 | Kim et al. .................. 606/250 |
| 7,744,632 B2 | 6/2010 | Usher |
| 8,246,657 B1* | 8/2012 | Samuel .................. 606/250 |
| 2002/0035366 A1 | 3/2002 | Walder |
| 2002/0143327 A1 | 10/2002 | Shluzas |
| 2003/0004512 A1 | 1/2003 | Farris |
| 2003/0060823 A1 | 3/2003 | Bryan |
| 2003/0114853 A1 | 6/2003 | Burgess |
| 2004/0044344 A1 | 3/2004 | Winquist |
| 2004/0092930 A1 | 5/2004 | Petit |
| 2004/0116928 A1 | 6/2004 | Young |
| 2004/0133202 A1 | 7/2004 | Suzuki |
| 2004/0133203 A1 | 7/2004 | Young |
| 2004/0260285 A1 | 12/2004 | Steib |
| 2005/0080416 A1 | 4/2005 | Ryan |
| 2005/0080419 A1 | 4/2005 | Donath |
| 2005/0090821 A1 | 4/2005 | Berrevoets |
| 2005/0107789 A1 | 5/2005 | Sweeney |
| 2005/0228377 A1 | 10/2005 | Chao |
| 2006/0058789 A1 | 3/2006 | Kim |
| 2006/0064093 A1 | 3/2006 | Thramann |
| 2006/0084996 A1 | 4/2006 | Metz-Stavenhagen |
| 2006/0206114 A1 | 9/2006 | Ensign |
| 2006/0217712 A1 | 9/2006 | Mueller |
| 2006/0233597 A1 | 10/2006 | Ensign |
| 2006/0247622 A1 | 11/2006 | Maughan |
| 2006/0271051 A1 | 11/2006 | Berrevoets |
| 2007/0049932 A1 | 3/2007 | Richelsoph |
| 2007/0123860 A1* | 5/2007 | Francis et al. .................. 606/61 |

FOREIGN PATENT DOCUMENTS

| | | |
|---|---|---|
| EP | 0536066 A1 | 4/1993 |
| EP | 0596788 A1 | 5/1994 |
| EP | 0734688 A2 | 10/1996 |
| EP | 0793947 A1 | 9/1997 |
| EP | 0836836 A2 | 4/1998 |
| EP | 0878170 A2 | 11/1998 |
| EP | 0956829 A2 | 11/1999 |
| EP | 1093761 A2 | 4/2001 |
| EP | 1103226 A2 | 5/2001 |
| EP | 0746255 B1 | 9/2002 |
| FR | 2697742 A1 | 5/1994 |
| FR | 2781359 A1 | 1/2000 |
| FR | 2804314 A1 | 8/2001 |
| WO | WO-9101115 A1 | 2/1991 |
| WO | WO-9106254 A1 | 5/1991 |
| WO | WO-9311715 A1 | 6/1993 |
| WO | WO-9321847 A1 | 11/1993 |
| WO | WO-9400062 A1 | 1/1994 |
| WO | WO-9400066 A1 | 1/1994 |
| WO | WO-9406361 A2 | 3/1994 |
| WO | WO-9408530 A1 | 4/1994 |
| WO | WO-9414384 A2 | 7/1994 |
| WO | WO-9420048 A1 | 9/1994 |
| WO | WO-9502372 A2 | 1/1995 |
| WO | WO-9508298 A1 | 3/1995 |
| WO | WO-9513753 A1 | 5/1995 |
| WO | WO-9513754 A1 | 5/1995 |
| WO | WO-9513755 A1 | 5/1995 |
| WO | WO-9513756 A1 | 5/1995 |
| WO | WO-9525473 A1 | 9/1995 |
| WO | WO-9526687 A1 | 10/1995 |
| WO | WO-9528889 A1 | 11/1995 |
| WO | WO-9531147 A1 | 11/1995 |
| WO | WO-9535067 A2 | 12/1995 |
| WO | WO-9602200 A1 | 2/1996 |
| WO | WO-9628106 A1 | 9/1996 |
| WO | WO-9632070 A2 | 10/1996 |
| WO | WO-9636291 A1 | 11/1996 |
| WO | WO-9639090 A1 | 12/1996 |
| WO | WO-9639972 A1 | 12/1996 |
| WO | WO-9641582 A1 | 12/1996 |
| WO | WO-9706742 A1 | 2/1997 |
| WO | WO-9714368 A1 | 4/1997 |
| WO | WO-9723170 A1 | 7/1997 |
| WO | WO-9731579 A1 | 9/1997 |
| WO | WO-9731580 A1 | 9/1997 |
| WO | WO-9738640 A1 | 10/1997 |
| WO | WO-9743974 A1 | 11/1997 |
| WO | WO-9815233 A1 | 4/1998 |
| WO | WO-9817188 A1 | 4/1998 |
| WO | WO-9837824 A1 | 9/1998 |
| WO | WO-9843551 A1 | 10/1998 |
| WO | WO-9855038 A1 | 12/1998 |
| WO | WO-9900065 A1 | 1/1999 |
| WO | WO-9903415 A1 | 1/1999 |
| WO | WO-9909901 A1 | 3/1999 |
| WO | WO-9915094 A1 | 4/1999 |
| WO | WO-9918874 A1 | 4/1999 |
| WO | WO-9929248 A1 | 6/1999 |
| WO | WO-9949802 A1 | 10/1999 |
| WO | WO-9955246 A1 | 11/1999 |
| WO | WO-9955247 A1 | 11/1999 |
| WO | WO-9956652 A1 | 11/1999 |

(56) References Cited

FOREIGN PATENT DOCUMENTS

| | | |
|---|---|---|
| WO | WO-0006038 A1 | 2/2000 |
| WO | WO-0015125 A1 | 3/2000 |
| WO | WO-0015126 A1 | 3/2000 |
| WO | WO-0016710 A1 | 3/2000 |
| WO | WO-0021447 A1 | 4/2000 |
| WO | WO-0021477 A1 | 4/2000 |
| WO | WO-0025689 A1 | 5/2000 |
| WO | WO-0042930 A1 | 7/2000 |
| WO | WO-0048523 A1 | 8/2000 |
| WO | WO-0054681 A2 | 9/2000 |
| WO | WO-0057801 A1 | 10/2000 |
| WO | WO-0059387 A1 | 10/2000 |
| WO | WO-0062691 A1 | 10/2000 |
| WO | WO-0062692 A2 | 10/2000 |
| WO | WO-0072769 A1 | 12/2000 |
| WO | WO-0072770 A1 | 12/2000 |
| WO | WO-0076413 A1 | 12/2000 |
| WO | WO-0101872 A1 | 1/2001 |
| WO | WO-0101873 A1 | 1/2001 |
| WO | WO-0106939 A1 | 2/2001 |
| WO | WO-0106940 A1 | 2/2001 |
| WO | WO-0108574 A1 | 2/2001 |
| WO | WO-0110317 A1 | 2/2001 |
| WO | WO-0115612 A1 | 3/2001 |
| WO | WO-0119266 A1 | 3/2001 |
| WO | WO-0124718 A1 | 4/2001 |
| WO | WO-0139677 A1 | 6/2001 |
| WO | WO-0152756 A1 | 7/2001 |
| WO | WO-0152757 A1 | 7/2001 |
| WO | WO-0152758 A1 | 7/2001 |
| WO | WO-0154597 A1 | 8/2001 |
| WO | WO-0158369 A1 | 8/2001 |
| WO | WO-0167972 A2 | 9/2001 |
| WO | WO-0167973 A2 | 9/2001 |
| WO | WO-0178613 A1 | 10/2001 |
| WO | WO-0191656 A2 | 12/2001 |
| WO | WO-0200124 A1 | 1/2002 |
| WO | WO-0200125 A1 | 1/2002 |
| WO | WO-0200126 A1 | 1/2002 |
| WO | WO-0202024 A1 | 1/2002 |
| WO | WO-0209603 A1 | 2/2002 |
| WO | WO-0215766 A2 | 2/2002 |
| WO | WO-0230307 A2 | 4/2002 |
| WO | WO-0234149 A2 | 5/2002 |
| WO | WO-0234151 A2 | 5/2002 |
| WO | WO-0238060 A1 | 5/2002 |
| WO | WO-0238061 A1 | 5/2002 |
| WO | WO-0238063 A2 | 5/2002 |
| WO | WO-0241797 A1 | 5/2002 |
| WO | WO-0245606 A1 | 6/2002 |
| WO | WO-0245607 A1 | 6/2002 |
| WO | WO-02078517 A2 | 10/2002 |
| WO | WO-02091931 A1 | 11/2002 |
| WO | WO-03037198 A1 | 5/2003 |
| WO | WO03068087 A1 | 8/2003 |
| WO | WO-03099148 A2 | 12/2003 |
| WO | WO-2004010881 A1 | 2/2004 |
| WO | WO-2004021902 A1 | 3/2004 |
| WO | WO-2004039268 A1 | 5/2004 |
| WO | WO-2004039269 A2 | 5/2004 |
| WO | WO-2004096065 A1 | 11/2004 |
| WO | WO-2004110289 A1 | 12/2004 |
| WO | WO-2004112626 A2 | 12/2004 |

* cited by examiner

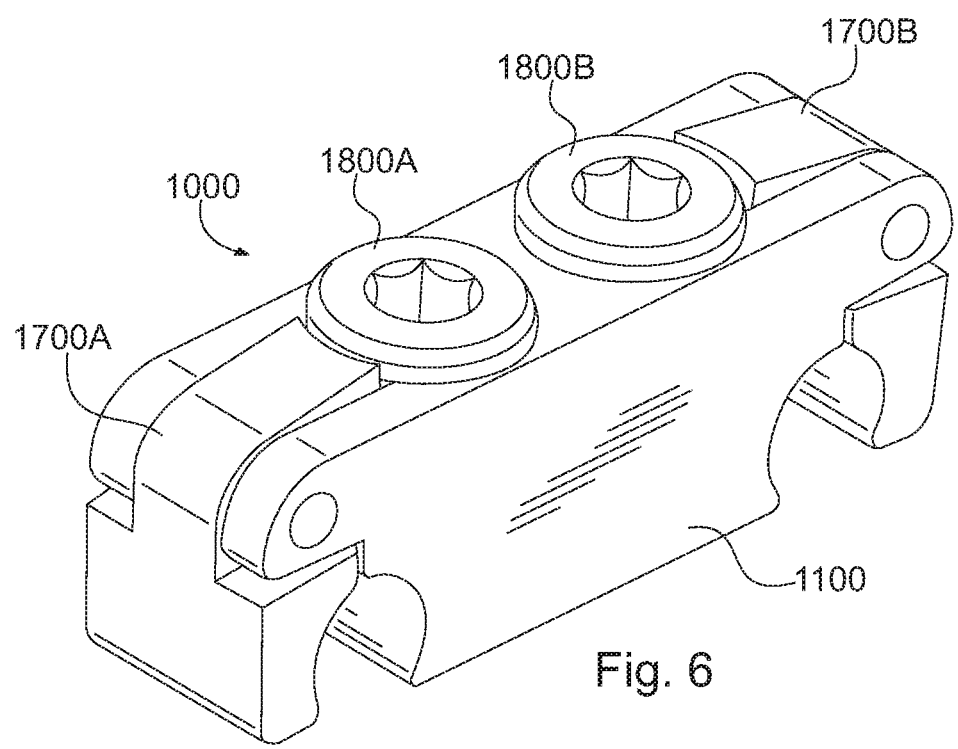

ROD TO ROD CROSS CONNECTOR

FIELD

The present invention relates generally to systems for stabilization and fixation the spine, and more particularly to an assembly for rigidly connecting two spinal rods together using one or more actuators in an arrangement that distributes clamping forces uniformly to the rods, and minimizes the transverse width of the assembly.

BACKGROUND

When performing a lateral or anterolateral corpectomy, the diseased or damaged vertebral body and adjacent disc are removed. Removal of the vertebral body and disc leaves a void in the spinal column. Therefore, a vertebral body replacement (VBR) device is placed into the void to provide support to the spinal column. Although the VBR device provides support, the spinal column can still be unstable, particularly in torsion or bending maneuvers. Therefore, surgeons often place a dual rod construct or other stabilization system over the affected level to provide additional stability. In a dual rod construct, pedicle screws are placed in the spine. Two rods are placed into the pedicle screws in parallel arrangement, and locked into the pedicle screws with set screws or other locking mechanisms.

The dual rod construct provides great stability in bending motions, but the spine can still be unstable in response to torsional movement. Therefore, additional devices are needed improve torsional stiffness. Various devices have been developed for rigidly connecting two spinal rods together to increase the stiffness of paired rods. These devices, sometimes referred to as rod to rod connectors, typically feature two or more set screws that must be tightened to connect the device to the rods. Each set screw must be tightened to connect the device to each rod. Tightening set screws can be tedious and time consuming, particularly when multiple rod to rod connectors are being connected to the rods.

U.S. Pat. No. 7,717,938 describes a rod to rod connector that utilizes a single set screw to connect both rods together. The rod to rod connector has an elongate body with two recesses for receiving rods. As the set screw is advanced into the elongate body, the set screw pushes two engagement members outwardly against the two rods. The set screw is advanced until the engagement members lock the rods in the recesses. The single set screw reduces the number of set screws on the connector by one, thereby reducing the amount of time and effort devoted to tightening set screws. Nevertheless, the device has a relatively large footprint due to the transverse width of the assembly. The elongate body must have a center portion large enough to contain not only the set screw, but also the two engagement members in a side by side fashion (see FIG. 1B). This adds to the overall transverse width of the assembly, which is not desirable. The placement of the engagement members inside the central body also limits the axial width of the engagement members, as they can only be as wide as the central body. If the central body is narrow, then the engagement members must be even narrower. If the engagement members are too narrow, they may not grip a large enough area of the rod to securely engage the rod.

SUMMARY

The drawbacks of conventional rod to rod cross connectors are resolved in many respects by rod to rod cross connectors in accordance with the present invention. Rod to rod connectors in accordance with the invention may include a central body and one or more actuators. The central body may be coupled to a first lever and a second lever. The first lever may include a free end separated from the central body by a first channel. The second lever may also include a free end separated from the central body by a second channel. The one or more actuators may be operable to pivot the first and second levers into a relatively closed position. When the first and second levers are in the relatively closed position, the free ends of the first and second levers are moved toward one another and toward the central body to contract the first and second channels. Drawing the first and second levers toward one another reduces the transverse width of the assembly, resulting in a smaller footprint after it is implanted.

BRIEF DESCRIPTION OF THE DRAWINGS

The foregoing summary and the following detailed description will be better understood in conjunction with the drawing figures, of which:

FIG. 6 is a perspective view of a rod to rod connector in accordance with another exemplary embodiment of the invention.

DETAILED DESCRIPTION OF PREFERRED EMBODIMENTS

Figure 1:
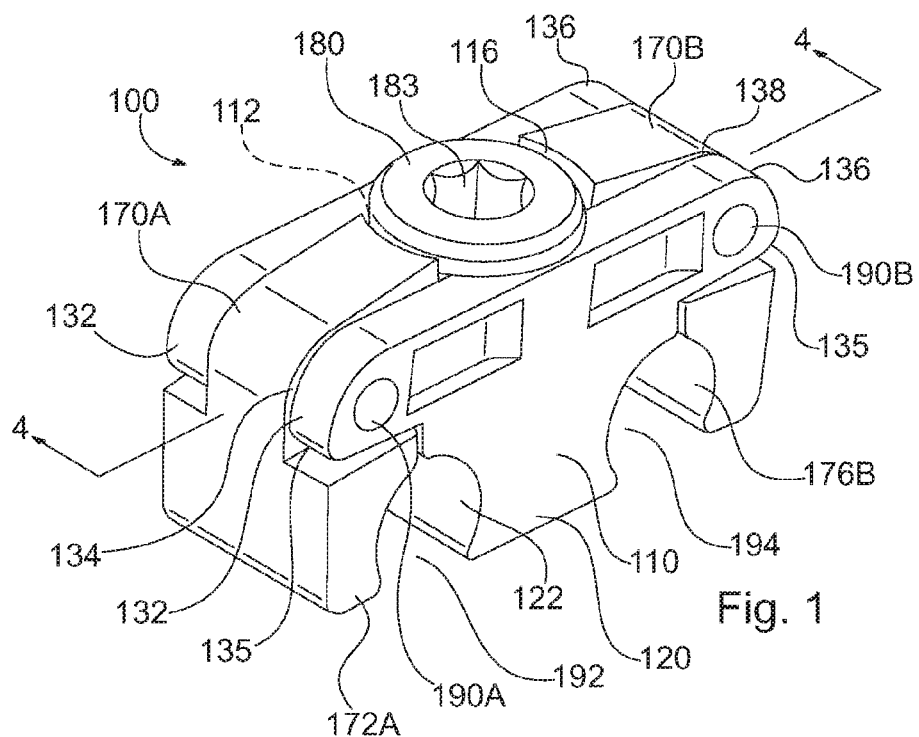
FIG. 1 is a perspective view of a rod to rod connector in accordance with one exemplary embodiment of the invention.

The term "axial", as used herein, means a direction parallel to the longitudinal axis defining a rod receiving channel in a rod to rod connector. For example, dimensions 191A and 191B in FIG. 2 extend in the axial direction and are referred to as axial widths. The long dimensions of pins 190A and 190B in FIG. 1 are also examples of dimensions extending in the axial direction relative to rod to rod connector 100.

The term "transverse", as used herein, means a direction perpendicular to the axial direction and parallel to a plane passing through the longitudinal axes of both rod channels. For example, dimension 121 in FIG. 3 extends in the transverse direction and is referred to herein as a transverse width.

Rod to rod cross connectors in accordance with the invention feature a central body and one or more clamping mechanisms that apply forces on rods to be connected. The clamping mechanism(s) apply forces on each rod in a direction toward the central body, so as to pull the rods into the central body, rather than push the rods outwardly and away from the central body. One or more actuators are used to engage the clamping mechanism(s) and apply force to the rods.

In a preferred embodiment, the cross connector may include a central body and one or more actuators. A first lever and a second lever may be coupled to the central body. The first lever may include a free end separated from the central body by a first channel. The second lever may also include a free end separated from the central body by a second channel. The one or more actuators may be operable to pivot the first and second levers into a relatively closed position. When the first and second levers are in the relatively closed position, the free ends of the first and second levers are moved toward one another and toward the central body to contract the first and second channels. Drawing the first and second levers toward one another reduces the transverse width of the assembly, as noted above.

The one or more actuators may consist of a single actuator. The central body may form a bore, and the actuator may be disposed in the bore. The actuator may include a first thread, and the bore may include a second thread. The actuator may be disposed in the bore with the first thread engaged with the second thread.

The actuator may include a shaft. In addition, the actuator may include a flange extending radially outwardly from the shaft. The actuator may also include a head extending radially outwardly from the shaft. The head and the flange may be separated from one another by an annular groove between the head and flange. The first and second levers may each comprise a tab extending into the groove between the head and flange on the actuator. A deformable member may be seated on the flange and extend in the groove. The deformable member may be a compression spring, lock washer or other deformable component. The deformable member may be compressed between the tabs and the flange to absorb excess force after the first and second levers are pivoted to a relatively closed position.

The central body may include a recess in communication with the bore. The recess may receive at least a portion of the head of the actuator. The head of the actuator may include a socket for receiving the tip on a driver. The central body may feature a T-shaped configuration that includes a base portion and a wing portion extending outwardly from the base portion.

The base portion may include a first concave wall section that partially defines the first channel, and a second concave wall section that partially defines the second channel. The free end of the first lever may include a third concave wall section that partially defines the first channel. The free end of the second lever may include a fourth concave wall section that partially defines the second channel. When the first and second levers are in the relatively closed position, the first and third concave wall sections may align with one another along a cylindrical profile, and the second and fourth concave wall sections may align with one another along a cylindrical profile.

The first wall section has an axial width substantially equal to the third wall section, and the second wall section has an axial width substantially equal to the fourth wall section. Compression forces applied by the first and second levers onto rods are distributed substantially evenly along the rods. Each lever may include an arm having a first axial width and a compression block having a second axial width. The second axial width may be greater than the first axial width.

The wing portion may include a first pair of extensions separated by a first slot, and a second pair of extensions separated by a second slot. The first slot may receive the arm of the first lever, and the second slot may receive the arm of the second lever. Each compression block may extend in at least one axial direction from its associated arm, forming at least one shelf that slidably engages at least one extension on the wing portion. The first lever may be pivotally coupled to the wing portion of the central body by a first pin, and the second lever may be pivotally coupled to the wing portion of the central body by a second pin.

Figure 2:
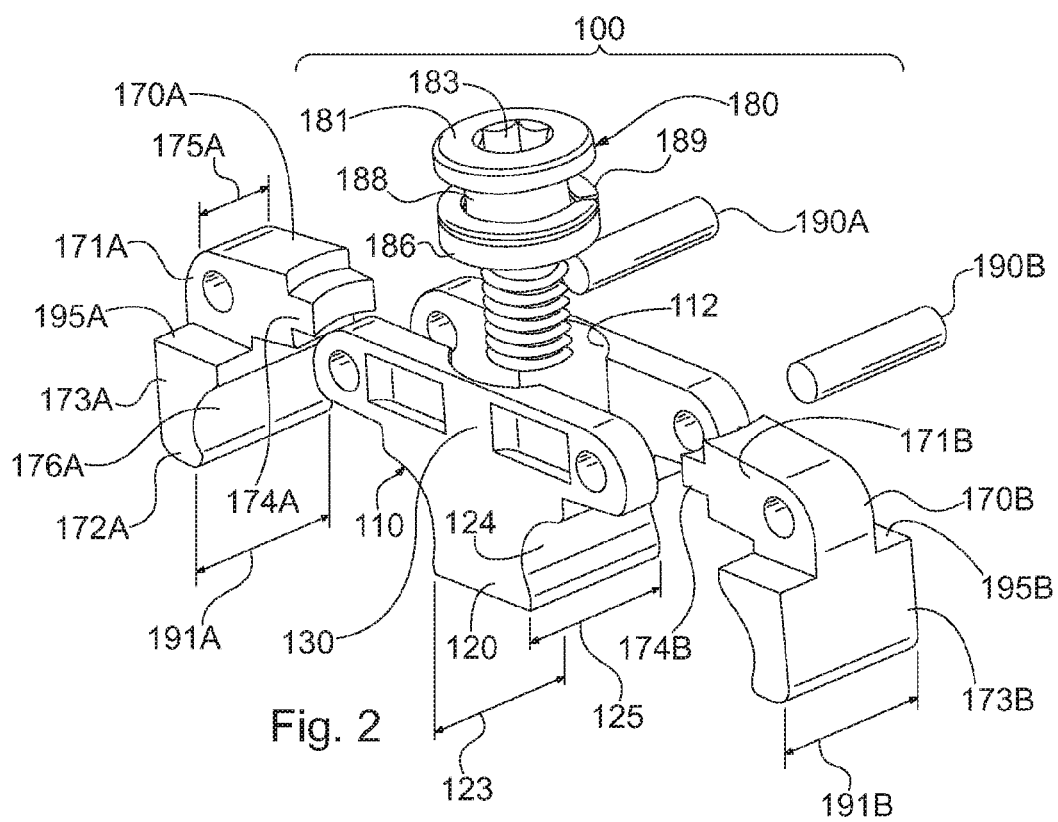
FIG. 2 is an exploded perspective view of the rod to rod connector of FIG. 1.

Referring to FIGS. 1 and 2, a cross connector 100 is shown in accordance with one exemplary embodiment. Cross connector 100 includes a central body 110 and a single actuator 180 that is operable to clamp the cross connector onto two spinal rods simultaneously. Central body 110 has a symmetrical shape.

Cross connector 100 includes a first lever 170A and a second lever 170B for clamping onto spinal rods. First lever 170A has a configuration that is identical to the configuration of second lever 170B. Therefore, features of first lever 170A will be described, with the understanding that identical features having the same description are present on second lever 170B. Features of first lever 170A are identified with reference numbers followed by the suffix "A". Corresponding features on second lever 170B that are shown in the drawings are labeled with the same reference number followed by the suffix "B". Some features of second lever 170B may be described, but any features of the second lever that are not expressly mentioned are nonetheless understood to be described by the description of the corresponding feature in first lever 170A.

First lever 170A and second lever 170B are pivotally coupled to central body. First lever 170A has an L-shaped body with a free end 172A. When first lever 170A is coupled to central body 110, free end 172A is separated from central body 110 by a first channel 192. Second lever 170B also has an L-shaped body with a free end 172B. When second lever 170B is coupled to central body 110, free end 172B is separated from central body 110 by a second channel 194. Actuator 180 is operable to pivot the first lever 170A and second lever 170B from a relative open position, shown in FIG. 3, to a relatively closed position, shown in FIG. 4. When first lever 170A and second lever 170B are in the relatively closed position, free end 172A of first lever 170A, and free end 172B of second lever 170B, are moved toward one another and toward the central body to contract the first channel 192 and second channel 194. Movement of the first and second levers toward one another reduces the transverse width of the assembly, resulting in a smaller footprint after it is implanted.

Central body 110 forms a bore 112 that extends through the midline of the central body as shown. Actuator 180 is disposed in bore 112, and has a first thread 182. Bore 112 includes a second thread 114. Actuator 180 is disposed in bore 112 with first thread 182 engaged with second thread 114. In this configuration, actuator 180 is displaceable through bore 112 in response to torque applied to the actuator. Actuator 180 includes a shaft 184 and a flange 186 extending radially outwardly from the shaft. A head 181 also extends radially outwardly from shaft 184. Head 181 and flange 186 are separated from one another by an annular groove 188 between the head and flange. First lever 170A has a tab 174A extending into groove 188 between the head and the flange on the actuator. Second lever 170B also has a tab 174B extending into groove 188. Tab 174A has an underside 178A, and tab 174B has an underside 178B. Flange 186 has a leading surface 187. Leading surface 187 is configured to apply force to undersides 176A and 176B when actuator 180 is reversed out of bore 112, as will be described in more detail below.

Torque is applied to the actuator to apply clamping force on the rods, as will be explained in more detail. Excessive torque can apply too much force to the rods and possibly damage the rods or create weakened areas. In addition, excessive torque applied to the actuator can cause damage to the threads on the actuator, the threads inside the clamping body, or other areas of the rod to rod connector. Therefore, it may be desirable to include one or more components that prevent damage to the rod and components of the rod to rod connector. For example, the rod to rod connector may include a deformable member between the actuator 180 and first and second levers 170A and 170B that absorbs excess forces before they are applied to the rods and inner engagement surfaces in the rod to rod connector. The deformable member may be in the form of one or more coil springs, spring washers or other compressible elements.

Figure 3:
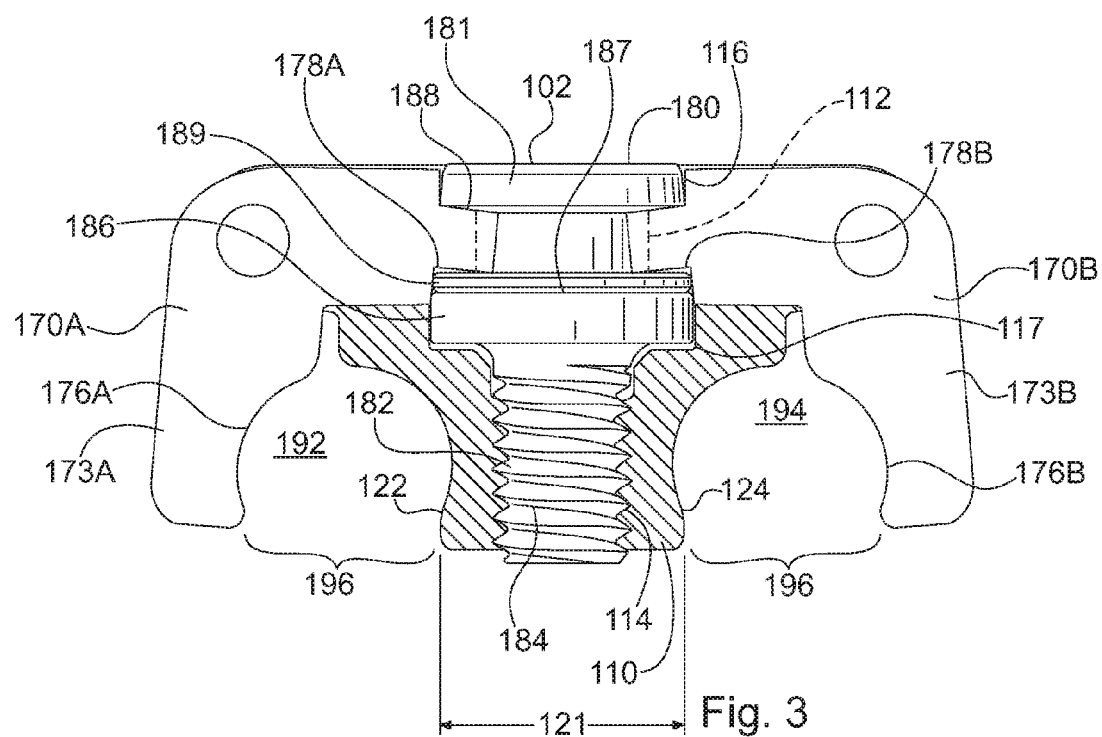
FIG. 3 is a cross sectional view of the rod to rod connector of FIG. 1, showing the rod to rod connector in a first condition.
Figure 4:
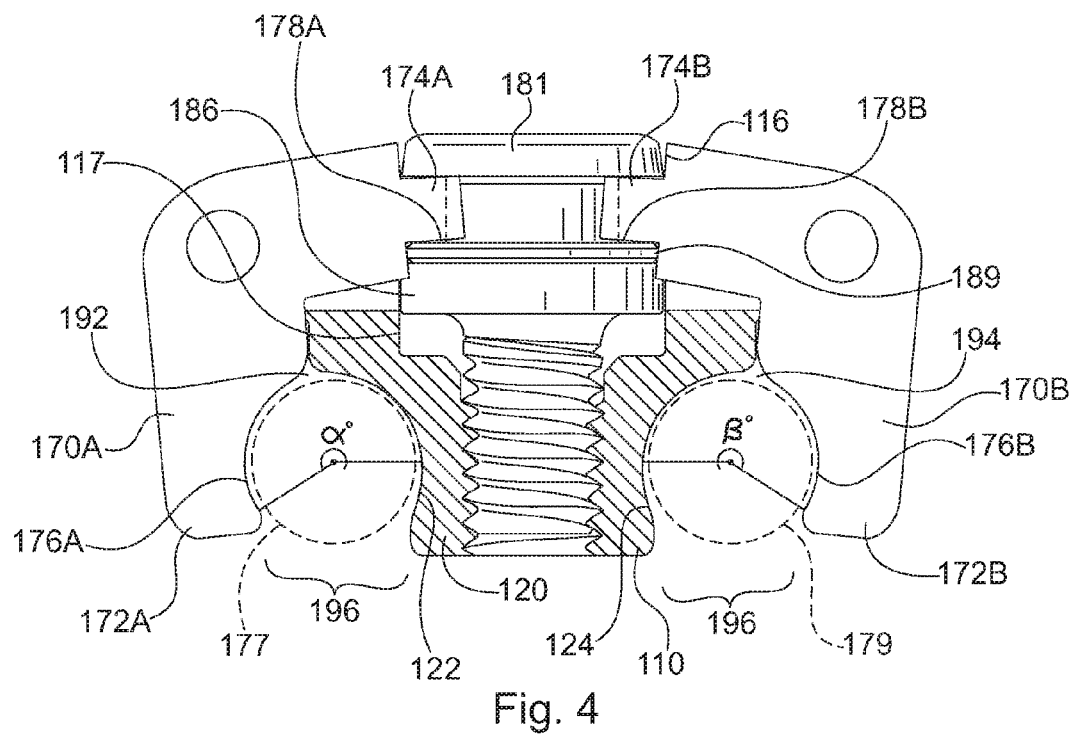
FIG. 4 is a cross sectional view of the rod to rod connector of FIG. 1, showing the rod to rod connector in a second condition, the cross sectional view corresponding to the view taken through line 4-4 of FIG. 1.

Referring to FIGS. 3 and 4, rod to rod connector 100 includes a deformable member in the form of a lock washer 189. Lock washer 189 is designed to provide a cushion between flange 186 and tabs 174A and 174B. When torque is applied to actuator 180, flange 186 bears upwardly against lock washer 189, tab 174A and tab 174B. The upward force on tab 174A pivots first lever 170A towards the relatively closed position, and the upward force on tab 174B pivots second lever 170B towards the relatively closed position. Once first lever 170A and second lever 170B reach the relatively closed position, the levers compress the rods against central body 110 in first and second rod channels 192 and 194.

The amount of torque applied to actuator 180 reaches a "threshold torque" once the first and second levers 170A and 170B are moved to the relatively closed position. Additional torque that is applied to the actuator beyond the threshold torque is excess torque. Lock washer 189 is compressible, allowing flange 186 and actuator 180 to continue moving in the bore in response to excess torque. As lock washer 189 is compressed, it absorbs the additional compression force created by the excess torque so that the additional force is not transferred to the rods.

The head 181 of actuator 180 has a disc shaped body that surrounds a central socket 183. Socket 183 is configured for receiving and mating with the tip of a torque applying tool, such as a driver. When central body 110 is coupled to first and second levers 170A and 170B, the central body and levers form a circular recess 116 in communication with bore 112. Recess 116 is configured and dimensioned to receive at least a portion of head 181. More preferably, recess 116 is configured and dimensioned to receive all of head 181 so that the head can be recessed inside central body 110. This provides a smooth, flat and continuous top surface 102 as shown in FIG. 3.

Central body 110 has a symmetrical T-shaped configuration featuring a base portion 120 and a wing portion 130 extending outwardly from the base portion. Base portion 120 includes a first concave wall section 122 that partially defines the first channel 192. Base portion 120 also includes a second concave wall section 124 that partially defines the second channel 194. Free end 172A of first lever 170A includes a third concave wall section 176A that partially defines the first channel 192. Free end 172B of second lever 170B includes a fourth concave wall section 176B that partially defines second channel 194. When first lever 170A and second lever 170B are in the relatively closed position, the first concave wall section 122 and third concave wall section 176A align with one another along a cylindrical profile 177. Similarly, second concave wall section 124 and fourth concave wall section 176B align with one another along a cylindrical profile 179.

Rod to rod connectors in accordance with the invention provide a distinct advantage over known rod to rod connectors, because of the ability to minimize the transverse width of the overall assembly. Rod to rod connector 100 applies inward clamping forces onto rods via the first and second levers 170A and 170B. Base portion 120 does not contain engagement members or other components that apply a clamping force outwardly to the rods. As such, the transverse width 121 of base portion 120 can be minimized, because the base portion and channel do not have to provide additional room to accommodate engagement components that move between the base portion and the rod channels. It should be understood that the transverse width of base portion 120, relative to the entire assembly, can be even smaller than what is shown in FIG. 3, because the walls around bore 112 can be made thinner. Smaller diameter actuators can also be selected to reduce the size of bore 112, and consequently, the transverse width of base portion 120.

Rod to rod connectors in accordance with the invention preferably distribute compression forces onto rods in an even, or substantially even, manner along each rod. Moreover, compression forces are preferably distributed over a wide section of each rod, rather than concentrated on small areas of the rod. Concentrated forces on small areas of a rod can create stress points on the rod. Applying forces over a larger area can increase the amount of frictional engagement between the rod to rod connector and the rods. To provide for greater distribution of force, levers in accordance with the invention preferably include sections having an enlarged axial width that applies force over a greater area of each rod. The enlarged axial width of each lever is preferably equal or substantially equal to the axial width of the central body.

For example, referring to FIG. 2, first concave wall section 122 has an axial width 123 equal to the axial width 191A of third concave wall section 176A. Second concave wall section 124 has an axial width 125 equal to the axial width 191B of fourth concave wall section 176B. In this configuration, the axial width of the rod engaged by central body 110 is the same as the axial width of rod engaged by the levers.

Rod to rod connectors in accordance with the invention preferably engage at least one half of the perimeter of each rod so as to distribute compression force over a large area of the rod. First concave wall section 122 and third concave wall section 176A collectively form a cylindrical engagement surface that spans an angle $\alpha$ of more than 180 degrees. Second concave wall section 124 and fourth concave wall section 176B also collectively form a cylindrical engagement surface spanning an angle $\beta$ of more than 180 degrees. In this configuration, the walls of rod channel 192 and rod channel 194 each engage more than one half of the perimeter of a rod. This provides a secure frictional engagement and distributes compression force evenly over a relatively large area of each rod.

Lever 170A includes an arm 171A having a first axial width 175A. Lever 170A also includes a compression block 173A having a second axial width equal to axial width 191A of first concave wall section 122. Axial width 191A of compression block 173A is greater than first axial width 175A of arm 171A. Compression blocks 173A and 173B each extend outwardly from their respective arms in axial directions, forming shelves 195A and 195B. In this configuration, the compression blocks 173A and 173B have an enlarged axial width, as compared to the arms, to apply compression force over a greater area of each rod.

Wing portion 130 includes a first pair of extensions 132 separated by a first slot 134, and a second pair of extensions 136 separated by a second slot 138. First slot 134 receives arm 171A of first lever 170A, and second slot 138 receives arm 171B of second lever 170B. First lever 170A is pivotally coupled to wing portion 130 by a first pin 190A, and second lever 170B is pivotally coupled to the wing portion by a second pin 190B. Shelves 195A and 195B slidably engage extensions 132 and 134 on wing portion 130. Wing portion 130 preferably includes rounded edges 135 along the perimeter of each of the extensions 132 and 136.

Figure 5:
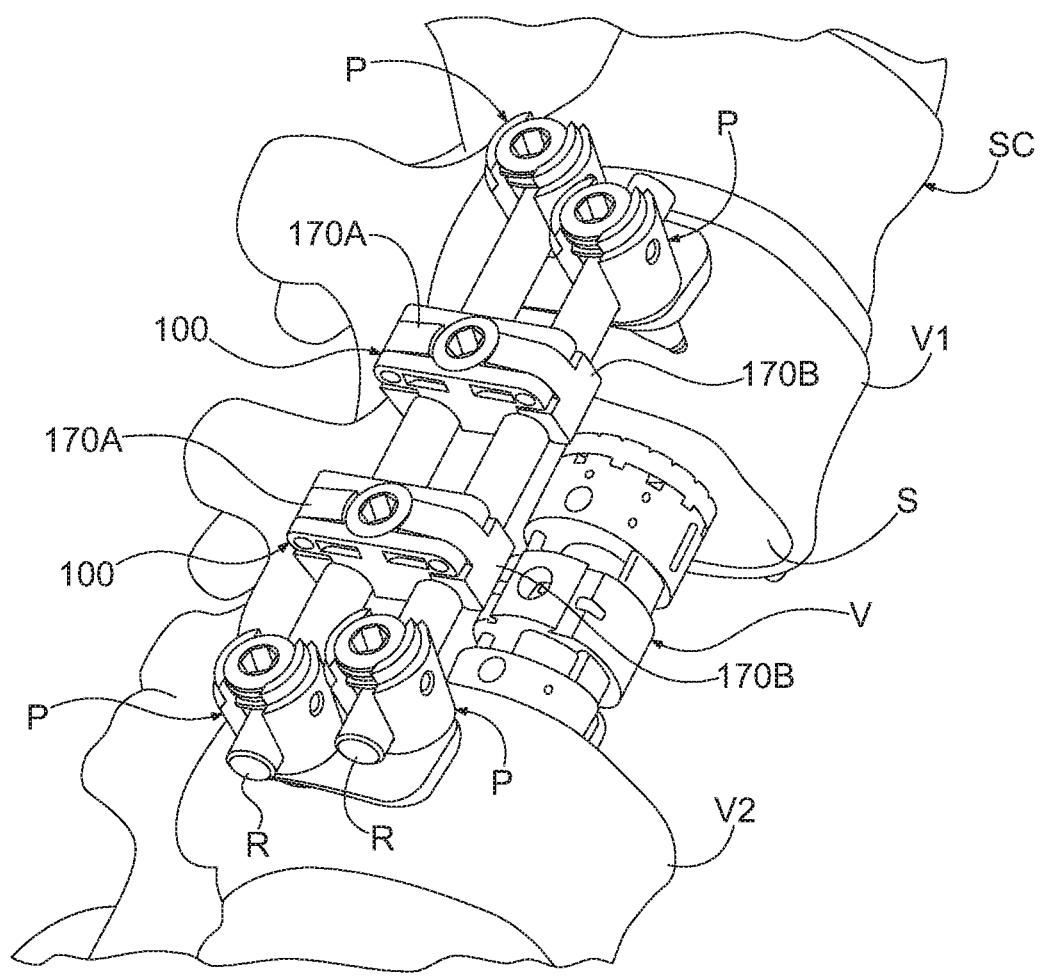
FIG. 5 is a perspective view of a rod pair interconnected by a pair of rod to rod connectors in accordance with the embodiment of FIG. 1, schematically shown in use after a corpectomy procedure.

FIG. 5 is a schematic illustration that shows how rod to rod connector 100 can be used in a spinal column SC after a corpectomy procedure. A vertebral body and disc material are removed from spinal column SC and replaced with a VBR implant V inside space S. VBR implant maintains the height of space S and is filled with bone graft or other osteogenic material to promote fusion of the adjacent vertebrae V1 and V2. To stabilize spinal column SC during fusion, a pair of rods R are secured to vertebral bodies V1 and V2 using pedicle screw implants P. Rods R are arranged parallel to one another, with each rod secured in two pedicle screw implants P. To enhance the stiffness of the rod construct, a pair of rod to rod connectors 100 are connected to rods R. Each rod to rod connector 100 extends with its long dimension generally perpendicular to rods R. Levers 170A and 170B of each rod to rod connector 100 are locked in the relatively closed position to clamp the rod to rod connectors to rods R. With this arrangement, rod to rod connectors 100 form transverse braces between rods R that increase the rigidity and stiffness of the rod pair.

A method of using rod to rod connector 100 will now be described. As noted above, first and second levers 170A and 170B are displaceable between the relatively open condition, shown in FIG. 3, and the relatively closed position, shown in FIG. 4. Each rod channel 192 and 194 spans an opening or "mouth" 196. The width of each mouth 196 increases as the levers are moved toward the relatively open position, and decreases as the levers are moved to the relatively closed position.

To connect two rods using rod to rod connector 100, first and second levers 170A and 170B are spread apart to the relatively open position. This can be done by applying torque to head 181 of actuator 180. Torque is applied to head 181 in a first direction to drive actuator 180 into bore 112. As actuator 180 is driven into bore 112, flange 186 is driven downwardly into a recess 117 in central body 110. Tabs 174A and 174B, which extend between head 181 and flange 186, are pushed downwardly by head 181, causing arms 171A and 171B to pivot and move compression blocks 173A and 173B upwardly and outwardly from central body 110. In this condition, the mouths 196 of each channel 192 and 194 are expanded so that the rods can easily slip into each channel.

Rod to rod connector 100 is lowered onto the two rods with base portion 120 positioned between the two rods, and levers 170A and 170B extending over the outside edges of the rods, as shown in FIG. 5. Once rod to rod connector 100 is seated on the rods, torque is applied to actuator 180 in a second direction opposite the first direction to drive the actuator in a reverse direction out of bore 112. As actuator 180 is reversed out of bore 112, flange 186 is driven upwardly out of recess 117 in central body. Tabs 174A and 174B are pushed upwardly by flange 186 and lock washer 189. This causes arms 171A and 171B to pivot and move compression blocks 173A and 173B downwardly and inwardly toward central body 110. Compression blocks 173A and 173B apply force to the rods in an inward direction, compressing the rods against central body 110 into a clamped condition. Torque is applied to actuator 180 in the second direction until the user detects resistance to further torque. Compressive force that results from excess torque is absorbed by lock washer 189, preventing possible damage to the rods.

Although the present invention has been described in connection with specific embodiments, it should be understood that the invention as claimed is not limited to the specific embodiments described herein. The specific embodiments described herein are provided only as examples. Various modifications may be made to the devices and methods described herein, including but not limited to various substitutions and combinations of device components and method steps, without departing from the scope of the invention.

For example, rod to rod connectors in accordance with the invention may have more than one actuator for moving the levers between the relatively open position and the relatively closed position. Two actuators may be provided, with each lever being controlled by its own actuator. This may be desired where the user wishes to control the amount of force applied to each rod individually. FIG. 6 shows a rod to rod connector 1000 with two actuators 1800A and 1800B. Actuator 1800A is configured to move a first lever 1700A and actuator 1800B is configured to move a second lever 1700B. The transverse width of central body 1100 is increased somewhat to accommodate the two actuators. Nevertheless, the transverse width of central body can still be kept relatively narrow, because it only needs to be wide enough to accommodate the two actuators, and does not have to provide additional width for engagement elements in the central body.

Rod to rod connectors in accordance with the invention may also include different actuator and lever configurations. In cross connector 100, actuator 100 is configured to move levers 170A and 170B toward the relatively closed position as the actuator is reversed out of central body 110. Cross connectors in accordance with the invention may have a different configuration that moves the levers toward the relatively open position when the actuator is reversed out of the central body. For example, the central body may include gears, levers or linkages that are connected between the actuator and lever to convert downward motion of the actuator into inward movement of the levers, so that the levers are moved to the relatively closed position as the actuator is driven into the central body.

Accordingly, it is intended that the appended claims cover all such variations of the devices, components and methods described herein.

What is claimed:

1. A cross connector for spinal rods, the cross connector comprising:
    a central body having a base portion and a wing portion extending away from the base portion, the wing portion including a first pair of extensions separated by a first slot and a second pair of extensions separated by a second slot;
    a first lever coupled to the central body, the first lever having an arm that is received in the first slot and a free end separated from the central body by a first channel;
    a second lever coupled to the central body, the second lever having an arm that is received in the second slot and a free end separated from the central body by a second channel; and
    an actuator operable to pivot the first and second levers into a relatively closed position in which the free ends are moved toward one another and toward the central body to contract the first and second channels.

2. The cross connector of claim 1, wherein the central body forms a bore, and the actuator is disposed in the bore.

3. The cross connector of claim 2, wherein the actuator comprises a first thread and the bore comprises a second thread, the actuator disposed in the bore with the first thread engaged with the second thread.

4. The cross connector of claim 1, wherein the actuator comprises a shaft and a flange extending radially outwardly from the shaft.

5. The cross connector of claim 4, wherein the actuator comprises a head extending radially outwardly from the shaft, the head and the flange separated from one another by an annular groove between the head and flange.

6. The cross connector of claim 5, wherein the first and second levers each comprise a tab extending into the groove between the head and the flange on the actuator.

7. The cross connector of claim 6, comprising a deformable member seated on the flange and extending in the groove.

8. The cross connector of claim 7, wherein the deformable member comprises a compression spring or a lock washer.

9. The cross connector of claim 7, wherein the deformable member is compressed between the tabs and the flange when the first and second levers are pivoted to the relatively closed position.

10. The cross connector of claim 5, wherein the central body comprises a recess in communication with the bore, the recess receiving at least a portion of the head of the actuator.

11. The cross connector of claim 5, wherein the head of the actuator comprises a socket for receiving the tip of a driver.

12. The cross connector of claim 1, wherein the central body comprises a T-shaped configuration.

13. The cross connector of claim 12, wherein the base portion comprises a first concave wall section that partially defines the first channel, and a second concave wall section that partially defines the second channel.

14. The cross connector of claim 13, wherein the free end of the first lever comprises a third concave wall section that partially defines the first channel, and wherein the free end of the second lever comprises a fourth concave wall section that partially defines the second channel.

15. The cross connector of claim 14, wherein, when the first and second levers are in the relatively closed position, the first and third concave wall sections align with one another along a cylindrical profile, and the second and fourth concave wall sections align with one another along a cylindrical profile.

16. The cross connector of claim 15, wherein the first concave wall section has an axial width substantially equal to the third concave wall section, and the second concave wall section has an axial width substantially equal to the fourth concave wall section, so that compression forces applied by the first and second levers onto rods are distributed substantially evenly along the rods.

17. The cross connector of claim 14, wherein the arm of each lever has a first axial width and a compression block having a second axial width, the second axial width greater than the first axial width.

18. The cross connector of claim 17, wherein each compression block extends in at least one axial direction from its associated arm, forming at least one shelf that slidably engages at least one extension on the wing portion.

19. The cross connector of claim 1, wherein the first lever is pivotally coupled to the wing portion of the central body by a first pin, and the second lever is pivotally coupled to the wing portion of the central body by a second pin.

20. A cross connector for spinal rods, the cross connector comprising:
a central body;
a first lever coupled to the central body, the first lever having a tab and a free end, the free end being separated from the central body by a first channel;
a second lever coupled to the central body, the second lever having a tab and free end, the free end being separated from the central body by a second channel; and
an actuator having a shaft, a head, and a flange, the head and the flange each extending radially away from the shaft,
wherein an annular groove is defined between the head and the flange,
wherein the tab of each of the first and second levers extends into the annular groove, and
wherein the actuator is operable to pivot the first and second levers into a relatively closed position in which the free ends are moved toward one another and toward the central body to contract the first and second channels.

21. The cross connector of claim 20, wherein the central body forms a bore, and the actuator is disposed in the bore.

22. The cross connector of claim 21, wherein the central body comprises a recess in communication with the bore, the recess receiving at least a portion of the head of the actuator.

23. The cross connector of claim 20, comprising a deformable member seated on the flange and extending in the groove.

24. The cross connector of claim 23, wherein the deformable member comprises a compression spring or a lock washer.

25. The cross connector of claim 23, wherein the deformable member is compressed between the tabs and the flange when the first and second levers are pivoted to the relatively closed position.

26. The cross connector of claim 20, wherein the head of the actuator comprises a socket for receiving the tip of a driver.

27. The cross connector of claim 20, wherein the central body comprises a base portion and a wing portion extending outwardly from the base portion.

28. The cross connector of claim 27, wherein the base portion comprises a first concave wall section that partially defines the first channel, and a second concave wall section that partially defines the second channel.

29. The cross connector of claim 28, wherein the free end of the first lever comprises a third concave wall section that partially defines the first channel, and wherein the free end of the second lever comprises a fourth concave wall section that partially defines the second channel.

30. The cross connector of claim 29, wherein, when the first and second levers are in the relatively closed position, the first and third concave wall sections align with one another along a cylindrical profile, and the second and fourth concave wall sections align with one another along a cylindrical profile.

31. The cross connector of claim 30, wherein the first concave wall section has an axial width substantially equal to the third concave wall section, and the second concave wall section has an axial width substantially equal to the fourth concave wall section, so that compression forces applied by the first and second levers onto rods are distributed substantially evenly along the rods.

32. The cross connector of claim 29, wherein each lever comprises an arm having a first axial width and a compression block having a second axial width, the second axial width greater than the first axial width.

33. The cross connector of claim 32, wherein the wing portion comprises a first pair of extensions separated by a first slot, and a second pair of extensions separated by a second slot, the first slot receiving the arm of the first lever, and the second slot receiving the arm of the second lever.

34. The cross connector of claim 33, wherein each compression block extends in at least one axial direction from its associated arm, forming at least one shelf that slidably engages at least one extension on the wing portion.

35. The cross connector of claim 27, wherein the first lever is pivotally coupled to the wing portion of the central body by a first pin, and the second lever is pivotally coupled to the wing portion of the central body by a second pin.

* * * * *